US010596139B2

(12) United States Patent
Chase et al.

(10) Patent No.: US 10,596,139 B2
(45) Date of Patent: *Mar. 24, 2020

(54) OXYBUTYNIN TRANSDERMAL THERAPEUTIC SYSTEM MUSCARINIC AGONIST COMBINATION

(71) Applicant: CHASE PHARMACEUTICALS CORPORATION, Parsippany, NJ (US)

(72) Inventors: Thomas N. Chase, Washington, DC (US); Kathleen E. Clarence-Smith, Washington, DC (US)

(73) Assignee: Chase Pharmaceuticals Corporation, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/556,206

(22) PCT Filed: Mar. 4, 2016

(86) PCT No.: PCT/US2016/020815
§ 371 (c)(1),
(2) Date: Sep. 6, 2017

(87) PCT Pub. No.: WO2016/144719
PCT Pub. Date: Sep. 15, 2016

(65) Prior Publication Data
US 2018/0050008 A1 Feb. 22, 2018

Related U.S. Application Data

(60) Provisional application No. 62/129,279, filed on Mar. 6, 2015, provisional application No. 62/144,010, filed on Apr. 7, 2015, provisional application No. 62/166,430, filed on May 26, 2015.

(51) Int. Cl.
A61K 31/216 (2006.01)
A61K 45/06 (2006.01)
A61K 31/439 (2006.01)
A61K 31/4439 (2006.01)
A61K 9/70 (2006.01)

(52) U.S. Cl.
CPC .......... *A61K 31/216* (2013.01); *A61K 9/703* (2013.01); *A61K 31/439* (2013.01); *A61K 31/4439* (2013.01); *A61K 45/06* (2013.01); *A61K 2300/00* (2013.01)

(58) Field of Classification Search
None
See application file for complete search history.

(56) References Cited

U.S. PATENT DOCUMENTS 6,562,368 B2 * 5/2003 Hsu ............... A61K 9/0014
424/443
8,404,701 B2 3/2013 Chase et al.
8,877,768 B2 11/2014 Chase
9,044,472 B2 6/2015 Chase
9,192,591 B2 11/2015 Chase
9,278,092 B2 3/2016 Chase
9,561,218 B2 2/2017 Clarence-smith
9,744,161 B2 8/2017 Chase
9,896,416 B2 2/2018 Clarence-smith
9,913,836 B2 3/2018 Clarence-smith
9,943,508 B2 4/2018 Chase
10,149,828 B2 12/2018 Chase
10,195,187 B2 2/2019 Chase
10,307,409 B2 6/2019 Chase
2007/0053995 A1 3/2007 Paborji
2011/0245294 A1* 10/2011 Paborji ........... A61K 31/137
514/305
2015/0030667 A1* 1/2015 Kaufman ......... A61K 31/713
424/450
2018/0116979 A1 5/2018 Clarence-smith
(Continued)

FOREIGN PATENT DOCUMENTS

WO WO9429303 A1 12/1994

OTHER PUBLICATIONS

Chase et al, "High Dose Donepezil Treatment of Alzheimer's Disease—Preliminary Results from CPC-201 and CPC-212 Trials", http://www.chasepharmaceuticals.com/blog/high-dose-donepezil-treatment-of-alzheimers-disease-poster-presented-on-december-9-by-thomas-n.-chase-md (Dec. 2015).

(Continued)

Primary Examiner — Jared Barsky
(74) Attorney, Agent, or Firm — Roy Issac

(57) ABSTRACT

Pharmaceutical compositions and combinations containing a muscarinic receptor antagonist, such as oxybutynin in a transdermal therapeutic system, and a muscarinic receptor agonist, optionally with an acetyl cholinesterase inhibitor, and methods of using the same for treatment of hypocholinergic disorders of the central nervous system such as Alzheimer type dementia. The respective pharmaceutical compositions and combinations of the present invention allow for safe administration of high doses of muscarinic receptor agonist, and improved efficacy of the muscarinic receptor agonist for treatment of hypocholinergic disorders of the central nervous system. The pharmaceutical compositions and combinations also allow for a maximum supply of acetylcholine to the central nervous system, when an acetyl cholinesterase inhibitor is used in combination with a muscarinic receptor antagonist and a muscarinic receptor agonist.

6 Claims, No Drawings

(56) References Cited

U.S. PATENT DOCUMENTS

2019/0091214 A1 3/2019 Chase
2019/0269627 A1 9/2019 Clarence-smith

OTHER PUBLICATIONS

D. R. Staskin et al., Effect of oxybutynin transdermal system on health-related quality of life and safety in men with overactive bladder and prostate conditions, International Journal of Clinical Practice, 2008, vol. 62, pp. 27-38.

* cited by examiner

OXYBUTYNIN TRANSDERMAL THERAPEUTIC SYSTEM MUSCARINIC AGONIST COMBINATION

CROSS-REFERENCE TO RELATED APPLICATIONS

This application is a National Stage of International Application No. PCT/US2016/020815 filed Mar. 4, 2016, which claims benefit of U.S. Provisional Application No. 62/166,430, filed May 26, 2015; U.S. Provisional Application No. 62/144,010, filed Apr. 7, 2015; and U.S. Provisional Application No. 62/129,279, filed Mar. 6, 2015; the entire disclosures of each of which are hereby incorporated herein by reference.

FIELD OF THE INVENTION

The invention pertains to the field of the treatment of hypocholinergic disorders of the central nervous system, in particular of Alzheimer type dementia, and to a new combination of an agonist and of an antagonist of the same receptor. More particularly, the invention is a combination of a muscarinic cholinergic receptor antagonist, selected from the group consisting of oxybutynin and pharmaceutically acceptable salts and solvates thereof in a transdermal therapeutic system, and a muscarinic cholinergic receptor agonist consisting of a Cholinergic Receptor Agonist (CRA).

Definitions

"Peripheral": refers to anticholinergic agents that are largely unable (have a limited ability) to enter the central nervous system following systemic administration and thus do not affect brain function to a clinically appreciable degree. These drugs can include both quaternary and tertiary ammonium anticholinergic agents, especially those having low lipid solubility.

"Anticholinergic therapy": the treatment with an anticholinergic agent of such medical conditions as gastro-intestinal cramping, nausea, retching, vomiting, fecal incontinence, bladder spasms, urinary incontinence, overactive bladder, asthma, motion sickness, muscular spasms, and smooth muscle contractive disorders; or the treatment with an anticholinergic agent of side effects caused by CRAs, including, but not limited to, gastro-intestinal cramping, nausea, retching, vomiting, fecal incontinence, bladder spasms, urinary incontinence, overactive bladder, asthma, motion sickness, muscular spasms, and smooth muscle contractive disorders.

"CNS": Central Nervous System.

"AChR": Acetylcholine Receptor.

"mAChRs": muscarinic acetyl choline receptors, muscarinic cholinergic receptors or muscarinic type receptors. Five subtypes of muscarinic receptors, M1 through M5, have been identified.

"CRA": Cholinergic Receptor Agonist (or muscarinic cholinergic receptor agonist) acting on the mAChRs, including orthosteric activators and allosteric activators, in particular both allosteric agonists and positive allosteric modulators, of mAChR subtypes.

"PNS": Peripheral Nervous System.

"CSF": Cerebrospinal Fluid.

"IR": Immediate Release of the active ingredient from a composition.

"ER": Extended Release (or sustained or controlled release) of the active ingredient from a composition by any administration route.

"AChEI(s)": Acetyl Choline Esterase Inhibitor(s).

"NsPAChA(s)": non-selective, peripheral AntiCholinergic Agent(s).

"Non selective": refers to nsPAChAs, and applies to anticholinergic agents exhibiting inhibitory activity broadly across the various subtypes of muscarinic M-receptors, namely the M1-M5 receptors.

"Transdermal delivery": administration of a drug that can be targeted to skin tissues just under the skin, regional tissues or organs under the skin, systemic circulation, and/or the central nervous system.

"Transdermal therapeutic system" a form of drug administration that is targeted to delivery of said drug to skin tissues just under the skin, regional tissues, using transdermal drug formulations and transdermal patches incorporating such transdermal drug formulations.

BACKGROUND OF THE INVENTION

Reduced levels of neurotransmitters including acetylcholine occur in dementias of the Alzheimer type. In particular, a deficit in acetylcholine-mediated transmission is thought to contribute to the cognitive and neurobehavioral abnormalities associated with these disorders. Accordingly, drugs known to augment cholinergic transmission in the CNS are the mainstay of current therapy. In addition, other diseases of the nervous system also involve decreased cholinergic transmission and are referred to as "hypocholinergic syndromes of the nervous system." Such diseases include, but are not limited to, Mild Cognitive Impairment (MCI), Lewy Body Disease dementia (LBD), Parkinson disease dementia (PDD), post-stroke dementia, vascular dementia, Traumatic Brain Injury, Down's syndrome, Anorexia Nervosa, and schizophrenia. It is well documented that schizophrenic patients experience cognitive disturbances that are not well addressed by current medications (reviewed in Foster et al, 2014). CRAs have been reported to dose-dependently improve the cognitive disturbances associated with schizophrenia, but the effect of CRAs is of limited extent and dose-dependent side effects prevent further increases in the CRA doses.

Acetylcholinesterase inhibitors (AChEIs) are now not only part of the standard of care for patients suffering from a dementia of the Alzheimer type, but are also widely used off-label for various other chronic progressive hypocholinergic disorders of the nervous system. AChEIs have the enhancement of acetylcholine-mediated neurotransmission as a general mechanism of action. All act in the human CNS to increase and prolong the availability of acetylcholine by inhibiting its degrading enzyme, acetylcholinesterase (AChE). Four AChEIs have been approved by the U.S. FDA for the treatment of dementias of the Alzheimer type: tacrine, donepezil [Aricept®], rivastigmine [Exelon®] and galantamine [Razadyne®]. Rivastigmine has also been approved for the treatment of Parkinson's disease dementia. AChEIs are available in various formulations including immediate release forms such as tablets, capsules and solutions as well as rapid dissolving and extended release forms for oral administration as well as those for parenteral (e.g. transdermal) administration.

Unfortunately, however, none of the currently available AChEIs offers more than modest clinical benefit for patients suffering from any of the aforementioned dementing disorders, even when these medications are administered at their maximum safe and tolerated doses. This is the first problem limiting the success of current AChEI therapy of Alzheimer type dementias.

A second problem limiting the success of current AChEI therapy of Alzheimer type dementias is that, even at recommended amounts, all these drugs produce dose limiting adverse reactions, mainly if not exclusively, by over-stimulating peripheral cholinergic receptors of the muscarinic type. As a result, signs and symptoms of untoward gastrointestinal, pulmonary, cardiovascular, urinary, and other systems dysfunction occur. These side effects commonly include, anorexia, nausea, vomiting, diarrhea, abdominal pain, weight loss; increased bronchial secretions, dyspnea, bronchoconstriction and bronchospasm; bradycardia, supraventricular cardiac conduction abnormalities, vasodilation, hypotension, dizziness and syncope; urinary bladder spasm, increased urinary frequency, and incontinence; flushing and diaphoresis; fatigue, headache, lachrymation, miosis, and loss of binocular vision (Physicians' Desk Reference 2008, Thomson PDR, Montvale, N.J.).

These problems linked to the use of the AChEIs have been solved by combining said AChEI with a nsPAChA (U.S. Pat. No. 8,404,701, the disclosure of which is incorporated herein in its entirety) or with a non-anticholinergic antiemetic agent (U.S. Pat. No. 8,877,768, the disclosure of which is incorporated herein in its entirety), these combinations allowing a great increase of the administered AChEI doses with attending increase in plasma and brain concentrations of the AChEI, and consequent possibility of increasing anti-dementia efficacy.

Another way to increase the cholinergic transmission in the brain is to stimulate post-synaptic cholinergic receptors by administering an agonist of the muscarinic receptors, but the results were generally disappointing. However, the efficacy of one such product, xanomeline, that stimulates muscarinic receptors in the brain and in the periphery was studied in patients with Alzheimer disease in a 6-month double-blind, placebo-controlled, parallel group trial. Compared to placebo, xanomeline was shown to significantly improve cognitive and behavioral symptoms of Alzheimer disease (Bodick et al., Arch. Neurol., 54: 465-473, (1997), which is incorporated herein in its entirety), but also caused dose-dependent unacceptable side effects, including bradycardia, gastro-intestinal distress, excessive salivation, and sweating. Such side effects prevented the use of doses of xanomeline that could achieve maximum anti-dementia efficacy and reflect stimulation of cholinergic receptors outside the brain. As described in the present invention, utilizing a drug that can antagonize the dose-limiting adverse events of a CRA without preventing anti-dementia efficacy enables the full antidementia efficacy of the CRA.

Dose-limiting adverse events attending the use of drugs that stimulate cholinergic transmission, such as xanomeline and other CRAs, appear to primarily reflect the excessive stimulation of peripheral cholinergic receptors, especially those of the muscarinic type (mAChRs), such that in both healthy volunteers and Alzheimer's patients many of these side effects have been reported for xanomeline; in the patient population this led to a discontinuation rate higher than 50% while the effects on cognition were not as robust and mainly seen at the highest doses tested (Mirza et al. CNS Drug Reviews Vol. 9, No. 2, pp. 159-186, 2003). In this review, the authors report that the maximal tolerated dose of orally administered xanomeline is 75 mg three times/day, i.e. 225 mg/day, even though some individuals tolerated a dose of 110 mg three times/day, taken with food. These authors also suggest that xanomeline would be a good antipsychotic.

In conclusion, the development of all of the above CRAs was discontinued because the results of the studies were disappointing not for a basic muscarinic inactivity of the products but because said products were inefficacious in patients and, in addition, induced dose-limiting, irreducible adverse effects.

In a review published in NEUROLOGY, 49, July 1997, by H. Robert Brashear, MD, of the book "Muscarinic Agonists and the Treatment of Alzheimer Disease" (Edited by Abraham Fisher—R. G. Landes, 1996), the reviewer concluded his comment as follows: "It will be of interest to most clinicians who treat Alzheimer's disease and valuable to chemical researchers, basic neuroscientists, biochemists, and pharmacologists investigating cholinergic dysfunction and therapy". Despite this clear interest and the extensive studies made on a series of compounds during the last two decades, none of the studied compounds became a drug for the treatment this disease for the reasons set forth above.

In addition, CRAs consisting of allosteric modulators of the $M_1$-muscarinic acetylcholine receptor are extensively studied and are the object of copious patent and scientific literature.

A review by B. J. Melancon, J. C Tarr, J. D. Panarese, M. R. Wood and C. W. Lindsley published in Drug Discovery Today; Volume 18, Numbers 23/24, December 2013, "Allosteric modulation of the $M_1$ muscarinic receptor: improving cognition and a potential treatment for schizophrenia and Alzheimer's disease" (Melancon et al.), the disclosure of which is incorporated herein by reference in its entirety, illustrates the role of the $M_1$ receptor in Alzheimer's disease and in schizophrenia by referring to selected allosteric modulators of the $M_1$ receptor.

This review also reports that the positive allosteric modulator MK-7622 entered Phase II clinical trials as an adjunct therapy to AChEIs in patients with AD. This positive allosteric modulator of the $M_1$ receptor, 3-[(1S,2S)-2-hydroxycyclohexyl]-6-[(6-methylpyridin-3-yl)methyl]benzo[h]quinazolin-4(3H)-one, is described in U.S. Pat. No. 8,883,810, the disclosure of which is incorporated herein by reference in its entirety.

Notwithstanding the previous aforementioned disappointing results and the recent progress of the scientific studies, the literature does not teach how to take advantage of the ubiquitous, potent activity of the muscarinic agonists safely. Thus, the problem of the effective and safe treatment of Alzheimer type dementia and in general of hypocholinergic disorders in the CNS such as schizophrenia, Down's syndrome, Tourette disease, tardive dyskinesia, Pick's disease, Huntington's chorea, and Friedrich's ataxia, with a muscarinic agonist, remains of primary importance.

An improvement in the treatment of Alzheimer type dementia is attained by a combined therapy associating a non-selective, peripheral anticholinergic agent, at a dose of from 20% to 200% the current daily doses, with an AChEI, at a dose up to about 6 times the maximal recommended dose of said AChEI. By such a treatment, a higher acetylcholinesterase inhibition in the CNS is achieved and greater relief of the symptoms of Alzheimer type dementia is enabled, by concomitantly decreasing concurrent adverse effects.

U.S. Pat. No. 8,877,768, discloses an improvement in the treatment of Alzheimer type dementia, which is attained by a combined therapy associating a non-anticholinergic-antiemetic agent, at a dose of from 50% to 300% the current IR daily doses, with an AChEI, at a dose up to 4 times the maximal recommended doses of said AChEI when administered alone.

Similarly, WO 2014/039637, the disclosure of which is herein incorporated by reference in its entirety, discloses increasing the blood levels of a concurrently administered AChEI with a non-selective peripheral anticholinergic agent, with the higher the dose of either the non-selective anticholinergic agent or the AChEI, the higher the increase of the AChEI blood levels. Thus, WO 2014/039637 uses high doses of both the non-selective, peripheral anticholinergic agent and of the AChEI in order to ameliorate the symptoms of Alzheimer's dementia. In particular, WO 2014/039637 states that "[W]hile potentially lessening side effects and thereby enabling the use of higher and thus more effective doses of the AChEI, merely employing the concomitant use of antiemetics, such as domperidone and others, or of anticholinergics such as propantheline, oxybutynin, tolterodine and others, falls short of achieving the utmost therapeutic advantages of AChEIs in the treatment Alzheimer type dementias".

However, U.S. Pat. No. 8,404,701 and, especially, WO 2014/039637, specifically exclude anticholinergic agents which are selective and/or non-peripheral because selective agents are not able to counteract the whole spectrum of the AChEIs' adverse effect and, worse, the non-peripheral anticholinergics, such as oxybutynin, are able to dangerously counteract the beneficial central action of said AChEIs.

Other literature discloses pharmaceutical compositions and Transdermal Therapeutic Systems (TTS) delivering oxybutynin through the human skin.

For example, U.S. Pat. Nos. 5,441,740 and 5,500,222, the disclosures of which are herein incorporated by reference in their entirety, disclose a patch for the transdermal administration of oxybutynin base using a monoglyceride or a mixture of monoglycerides of fatty acids as skin permeation-enhancer.

U.S. Pat. Nos. 5,686,097; 5,747,065; 5,750,137 and 5,900,250, the disclosures of which are herein incorporated by reference in their entirety, disclose a patch for the transdermal administration of oxybutynin base using a monoglyceride or a mixture of monoglycerides plus a lactate ester as skin permeation-enhancer.

A similar patch, adding a non-rate controlling tie layer on the skin-proximal surface of the reservoir, not affecting the drug release, is described in U.S. Pat. Nos. 5,614,211 and 5,635,203, the disclosures of which are herein incorporated by reference in their entirety.

U.S. Pat. Nos. 5,212,199, 5,227,169, 5,601,839 and 5,834,010, the disclosures of which are herein incorporated by reference in their entirety, disclose a patch for transdermal administration of basic drugs using triacetin as permeation enhancer.

U.S. Pat. No. 6,555,129, the disclosure of which is herein incorporated by reference in its entirety, discloses a TTS substantially consisting of an oxybutynin-containing matrix mass in the form of a layer which is self-adhesive, and in which the matrix mass consists of ammonium-group-containing (meth)acrylate copolymers, at least one citric acid triester and 5-25% by weight of oxybutynin.

U.S. Pat. No. 6,562,368, the disclosure of which is herein incorporated by reference in its entirety, discloses a method for transdermally administering oxybutynin using a composition in form of a patch, a cream, a gel, a lotion or a paste comprising oxybutynin and a hydroxide-releasing agent substantially consisting of inorganic hydroxides, inorganic oxides, metal salts of weak acids, and mixtures thereof.

U.S. Pat. Nos. 6,743,441; 7,081,249; 7,081,250; 7,081,251; 7,081,252 and 7,087,241, the disclosures of which are herein incorporated by reference in their entirety, disclose a transdermal patch delivering a composition comprising oxybutynin to a subject to provide a plasma area under the curve ratio of oxybutynin to an oxybutynin metabolite of from about 0.5:1 to about 5:1, optionally in the presence of a permeation enhancer.

U.S. Pat. Nos. 7,029,694; 7,179,483; 8,241,662 and US 2009/0018190, the disclosures of which are herein incorporated by reference in their entirety, disclose a transdermal gel formulation comprising oxybutynin providing a plasma area under the curve ratio of oxybutynin to an oxybutynin metabolite of from about 0.5:1 to about 5:1, optional in the presence of a permeation enhancer.

US 2004/0219194, the disclosure of which is herein incorporated by reference in its entirety, discloses a transdermal therapeutic system containing oxybutynin, triacetin and Aloe vera extract as permeation enhancer.

US 2004/0057985, the disclosure of which is herein incorporated by reference in its entirety, discloses transdermal therapeutic systems (TTS) for the administration of oxybutynin with which therapeutically active absorption rates can be achieved without the necessity of adding permeation-enhancing substances. These TTS comprise a substantially water vapor-impermeable backing layer, at least one pressure-sensitive adhesive matrix layer attached thereto, and a detachable protective film, said matrix layer comprising an inner phase containing the active substance oxybutynin, and an outer, pressure sensitive adhesive phase based on hydrocarbon polymers or/and silicone polymers.

US 2005/0064037, the disclosure of which is herein incorporated by reference in its entirety, discloses an oxybutynin gel formulation topical gel formulation comprising oxybutynin chloride salt, a short chain alcohol, a gelling agent substantially consisting of high-molecular-weight, cross-linked polymer of acrylic acid or cross-linked copolymer of acrylic acid and $C_{10-30}$ alkyl acrylate, and optionally a permeation enhancer substantially consisting of propylene glycol, propylene glycol laurate, isopropyl myristate, and methyl lactate.

WO 2005/039531, US2007/022379, US 2010/0216880, US 2014/0037713 and U.S. Pat. No. 8,652,491, the disclosures of which are herein incorporated by reference in their entirety, disclose a transdermal or transmucosal pharmaceutical formulation, that can be utilized for topical or transdermal application, such that solutions, creams, lotions, sprays, ointment, gels, aerosols and patch devices, for the delivery of one or more active agents, including anticholinergics, in particular oxybutynin. Said formulation includes oxybutynin in a solvent system comprising a diethylene glycol monoalkyl ether and a glycol in specific ratios, alcohol and water. In particular, according to U.S. Pat. No. 8,652,491 a possible secondary active agent, in addition to the anti-cholinergic agent such as oxybutynin, may be an antiperspirant, a tranquilizer or another agent capable of ameliorating hyperhidrosis. In addition, according to WO 2005/039531 the active agent may also be selected from an anti-Alzheimer's drug, in particular galantamine, rivastigmine, donepezil, tacrine, or memantine, without giving any indication of the doses to be used.

WO 2005/107812, U.S. Pat. No. 7,425,340 and US 2008/0260842, the disclosures of which are herein incorporated by reference in their entirety, disclose formulations containing an anticholinergic agent, in particular oxybutynin, in admixture with urea, urea congeners or urea-containing compounds as permeation enhancers.

WO 01/07018 and U.S. Pat. No. 8,420,117, the disclosures of which are herein incorporated by reference in their entirety, disclose a matrix patch formulation containing no water for external use, comprising, as essential components oxybutynin hydrochloride, citric acid and sodium acetate.

WO2013/061969 and US 2014/0271796, the disclosures of which are herein incorporated by reference in their entirety, disclose a transdermal absorption preparation comprising at least one drug selected from oxybutynin and pharmaceutically acceptable salts thereof; and a sterol such as cholesterol, cholesterol derivatives and cholesterol analogs.

U.S. Pat. No. 8,802,134, the disclosure of which is herein incorporated by reference in its entirety, discloses a method for producing a patch wherein oxybutynin is incorporated in an adhesive agent layer composition comprises the acrylic-based polymer as the adhesive base agent, and the acrylic-based polymer is a copolymer of polymethyl methacrylate with a polyacrylate.

U.S. Pat. No. 8,877,235, the disclosure of which is herein incorporated by reference in its entirety, discloses a patch consisting of a support layer and of an adhesive agent layer arranged on the at least one surface of the support layer, the adhesive agent layer comprising oxybutynin hydrochloride in a supersaturated concentration in a dissolved form. Said layer also comprises acrylic-based polymers and rubber-based polymers, as adhesive base agents, and liquid paraffin, a sterol, an organic acid, and a tackifier.

The disclosures of the aforementioned documents are incorporated herein by reference in their entirety.

Oxybutynin is a well-known non-selective anticholinergic medication used to relieve urinary and bladder difficulties, including frequent urination and urge incontinence and all the above references emphasize this use. However, as set forth above, oxybutynin is not "peripheral" as per the definition given above because it is able to cross the blood brain barrier ("BBB") to a non-negligible extent (Rebecca J McCrery and Rodney A Appell, Ther Clin Risk Manag. March 2006; 2/1: 19-24).

Oxybutynin is commercially presented in a patch releasing 3.9 mg/day oxybutynin (OXYTROL®). This patch provides significant improvements in all the measured parameters with less systemic adverse effects, as summarized by J. Jayarajan and S. B. Radomski in a review presented on 4 Dec. 2013: "Pharmacotherapy of overactive bladder in adults: a review of efficacy, tolerability, and quality of life" (J. Jayarajan et al., Research and Reports in Urology 2014:6), the disclosure of which is herein incorporated by reference in its entirety. However, oxybutynin is deemed to cross the BBB owing to its high lipophilicity, neutrality, and small molecular size (C. A. Donnellan et al. BMJ 1997; 315:1363-4; R. Scheife and M. Takeda, Clin Ther. 2005; 27:144-53), the disclosure of which is herein incorporated by reference in its entirety.

Oxybutynin is also commercially presented (GELNIQUE®) in a TTS consisting of a hydroalcoholic gel containing 100 mg oxybutynin chloride per gram of gel and available in a 1 gram (1.14 ml) unit dose. This TTS is deemed to have a pharmacokinetic profile similar to that of the patch delivery system, while producing lower N-desetyloxybutynin metabolite plasma concentrations (Vincent R Lucente et al.; Open Access Journal of Urology 2011/3, 35-42). Another commercial TTS system presents oxybutynin in a hydroalcoholic gel containing 30 mg oxybutynin base per gram of gel and is available (ANTUROL®) in a 0.92 gram (1 mL) unit dose that contains 28 mg oxybutynin per gram of gel. Also Anturol® demonstrated plasma levels of oxybutynin comparable to the efficacious plasma levels observed for oral and patch therapies with lower N-desethyloxybutynin plasma levels (Anturol® Gel Summary by Antares Pharma).

Oxybutynin is a very good tool for administering anticholinergic therapy but, even when given by transdermal route, it is deemed to induce adverse effects in the CNS, as per the warning that is present in the OXYTROL® label, and as reported in the literature. Indeed the current FDA product label for transdermal oxybutynin (Oxytrol®) states that nervous system side effects of Oxytrol® may include: Very common (10% or more): Dizziness, somnolence; Common (1% to 10%): Headache, mental/mood changes (such as confusion), insomnia, nervousness, convulsions, dysgeusia; and frequency not reported: paralysis, coma, CNS excitation. It further lists Central Nervous System Effects under Warnings and Precautions: "Products containing oxybutynin are associated with anticholinergic central nervous system (CNS) effects. A variety of CNS anticholinergic effects have been reported, including headache, dizziness, and somnolence. Patients should be monitored for signs of anticholinergic CNS effects, particularly after beginning treatment." In addition, the label states that overdosage with oxybutynin has been associated with anticholinergic effects including CNS excitation and that CNS symptoms of overdose may include: memory loss, confusion, convulsions, dizziness, and drowsiness (severe). This possibility becomes a-priori, a material risk if it is intended to be used for the treatment of Alzheimer type dementia in combination with a CRA such as xanomeline, due to the competitive action of the two drugs inside the CNS.

U.S. Pat. No. 5,980,933, the disclosure of which is herein incorporated by reference in its entirety, discloses a transdermal xanomeline patch formulation comprising an effective amount of xanomeline, from 0.1 to 10 parts by weight azone, from 30 to 69.8 parts ethanol, 29 to 50 parts by weight water, from 0 to 30 parts by weight propylene glycol, and 1 to 5 parts by weight Klucel HF, also with about 70 to 99.8% acrylate adhesive. The literature only specifies that such a patch should have less adverse effects compared with the oral forms.

US 2011/0020423 discloses the combination of one or more muscarinic "Activators" (e.g., agonist, partial agonist, co-agonist, physiological agonist, potentiator, stimulator, allosteric potentiator, positive allosteric modulator or allosteric agonist) and one or more muscarinic "Inhibitors" (e.g., antagonist, partial antagonist, competitive antagonist, non-competitive antagonist, uncompetitive antagonist, silent antagonist, inverse agonist, reversible antagonist, physiological antagonist, irreversible antagonist, inhibitor, reversible inhibitor, irreversible inhibitor, negative allosteric modulator, or allosteric antagonist).

U.S. Pat. No. 8,853,219 discloses muscarinic agonists, which are useful for stimulating muscarinic receptors and treating cognitive disorders, said agonists including oxadiazole and oxathiazole derivatives, in particular 5-(3-ethyl-1,2,4-oxadiazol-5-yl)-1,4,5,6-tetrahydropyrimidine, also known as MCD-386, which is described in the literature for example in U.S. Pat. No. 5,403,845 to Dunbar, et al., 3-Methyl-5-(piperidin-3-yl)-1,2,4-oxadiazole), as a racemic mixture and as the single stereoisomers. This document also discloses combination compositions and co-administration comprising muscarinic agonists and antagonists, said muscarinic agonists including the substituted oxadiazoles and thiadiazoles disclosed therein and said muscarinic antagonists including atropine sulfate, N-methylatropine nitrate, flavoxate hydrochloride, N-methylscopolamine hydrochloride (methscopolamine), oxybutinin chloride, glycopyrrolate bromide, darifenacin hydrobromide, solifenacin succinate, propantheline bromide, trospium chloride, tolterodine tartrate, fesoterodine fumarate, methantheline bromide and combinations thereof. In terms of co-administration of a muscarinic-antimuscarinic combination, this document intends separate administration of agonist and antagonist, e.g., in separate dosage forms such as separate pills, separate injectable solutions or separate iontophoretic patches. According to this document, pharmacological tests made with a combination of representative oxadiazole muscarinic agonists with muscarinic antagonists showed that darifenacin and oxybutinin, both tertiary amines, are less effective than the other muscarinic antagonists by both oral and iontophoretic patch administration. In addition, this document observes that these drugs are known to penetrate the blood-brain barrier and may therefore inhibit the therapeutic effects of the agonist in the brain. Thus, this document, does not make any distinction among the peripheral/non-peripheral and selective/non-selective antimuscarinic agents.

In summary notwithstanding great scientific effort, the problem of the safe treatment of hypocholinergic disorders of the nervous system such as Parkinson's dementia, Lewy body diseases, Down Syndrome, and chronic neuropathic pain remains unsolved.

SUMMARY OF THE INVENTION

It has now been found that an oxybutynin transdermal system, when concurrently or sequentially administered in combination with a CRA, is able to neutralize the adverse effects that hindered the development of a muscarinic agonist for the treatment of central disorders due to a deficit of acetylcholine in the brain without inducing central nervous system anticholinergic effects. In fact, by treating a human with an oxybutynin transdermal system, it is possible to safely administer a centrally-acting CRA, even at high doses thus, in case of a patient suffering from Alzheimer type dementia, allowing said CRA to safely activate the acetylcholine receptors and to improve cognition.

In particular, by treating a human with an oxybutynin TTS, it is possible to safely administer a CRA to a patient suffering from hypocholinergic disorders of the central nervous system, such as AD, AD-type, Mild Cognitive Impairment (MCI), Lewy Body Disease dementia (LBD), Parkinson disease dementia (PDD), post-stroke dementia, vascular dementia, Traumatic Brain Injury, Anorexia Nervosa, Down's syndrome, Tourette disease, tardive dyskinesia, Pick's disease, Huntington's chorea, Friedrich's ataxia, chronic neuropathic pain and schizophrenia, thus allowing said CRA to safely activate the acetylcholine receptors and to improve cognition.

The finding of the present invention was unexpected in view of the disclosures of the prior art, in particular in view of the knowledge of, one side, the lack of efficacy of the muscarinic cholinergic receptor agonists at the doses administered to the patients and, on the other side, of the irreducible adverse affects induced by the products at said administered doses. On the contrary, it has been found that the administration of a CRA concurrently with an oxybutynin transdermal system, will not produce any adverse effect not only at the CRA doses normally administered to a human, but also at doses which would be unquestionably intolerable for said human.

The invention relates to a transdermal therapeutic system containing 4-diethylaminobut-2-ynyl 2-cyclohexyl-2-hydroxy-2-phenylethanoate, known under its International Non-proprietary name as oxybutynin, or a pharmaceutically acceptable salt thereof, for use in the treatment of Alzheimer type dementia, in combination with a CRA. The invention also concerns use of such a transdermal therapeutic system in a method for enhancing the maximal efficacy and maximal tolerated dose of a CRA in a patient suffering from dementia of the Alzheimer type or of other types of hypocholinergic disorders of the nervous system.

In particular, this finding eliminates the dose-limit that, in the past, caused the failure of all the clinical trials, thus providing a new tool for treating Alzheimer type dementia and in general central hypocholinergic disorders by enabling the full efficacy of CRAs. Said new tool comprises treating a patient in need of such a treatment with even a high dose of an oxybutynin transdermal system, in combination with a CRA. This treatment occurs, on one hand without the onset of CRA-associated peripheral dose-limiting adverse effects and, on the other hand, without the onset of oxybutynin central adverse effects.

Thus, the present invention provides a combination of an oxybutynin transdermal system and a CRA which is useful for the treatment of Alzheimer type dementia and for CNS hypocholinergic disorders. More particularly, in said combination said CRA is used at a dose that would have been intolerable in the absence of said oxybutynin transdermal system. In practice, said CRA may be present in said combination at a dose that is higher than the mean maximal tolerated dose which was determined during the clinical trials.

In addition, the present invention provides the combination of an oxybutynin transdermal system with a CRA, said combination being formulated in the same unit form, wherein the CRA is in a substantially high dose.

Finally, the present invention also provides the addition of an AChEI to the above oxybutynin transdermal system/CRA combination, thus assuring a maximum supply of acetylcholine to the CNS.

DETAILED DESCRIPTION

Thus, the present invention provides a pharmaceutical combination comprising, as Components:
(a) a muscarinic receptor antagonist selected from the group consisting of oxybutynin and pharmaceutically acceptable salts and solvates thereof in a TTS; and
(b) a muscarinic receptor agonist selected from the group consisting of cholinergic receptor agonists (CRA).

This combination may be used for the treatment of Alzheimer type dementia and more generally for hypocholinergic disorders of the central nervous system, including Parkinson's disease dementia, Frontotemporal Lobar Dementia, Mild cognitive Impairment (MCI), Vascular Dementia, Traumatic Brain Injury, Down's Syndrome, Anorexia nervosa, and Schizophrenia. The present invention provides a transdermal therapeutic system Component (a) that may be used for the treatment of hypocholinergic disorders of the central nervous system, including but not limited to, Alzheimer type dementia (including but not limited to Parkinson's disease dementia, and Frontotemporal Lobar Dementia), Mild cognitive Impairment (MCI), Vascular Dementia, Traumatic Brain Injury, Down's Syndrome, Anorexia nervosa, and Schizophrenia. This treatment is made in combination with a CRA composition Component (b) in form of an IR or ER oral formulation.

The Oxybutynin Transdermal Therapeutic System

The oxybutynin TTS used as Component (a) may be in any oxybutynin delivering transdermal pharmaceutical form, such as a patch, a gel, a cream, a spray, an ointment, a lotion or a paste, wherein oxybutynin is present in admixture with the common diluents and permeation enhancers. Said pharmaceutical form contains oxybutynin base or a pharmaceutically acceptable salt thereof, such as its hydrochloride, hydrobromide, sulfate, phosphate, mesilate, acetate, maleate, succinate, lactate, citrate, hydrogen tartrate, tartrate, napsilate or embonate.

The permeation enhancer may be any substance allowing the improved permeation of drugs through the skin (see for example the review in Pharmaceutical Technology, November 1997, pages 58-66, the disclosure of which is herein incorporated by reference in its entirety). These substances may be lower ($C_1$-$C_4$) alkanols; fatty alcohols such as lauryl alcohol (dodecanol), alone or in combination with a lower alkanol; fatty acids such as linolenic acid or oleic acid; fatty acid esters such as isopropyl palmitate, stearate, linoleate, oleate or myristate; glycerol; glycerol monoesters such as glycerol monostearate, monolinoleate or monooleate; glycerol diesters; glycerol triesters such as triacetin; sucrose monostearate, monolinoleate or monooleate; sorbitan esters; fatty alcohol ethers having from 10 to 20 carbon atoms; glycols, such as diethylene glycol or propylene glycol; glycols lower alkyl ethers, such as diethylene glycol mono ($C_2$-$C_4$)alkyl ether, in particular diethylene glycol monoethyl ether.

These permeation enhancers are present in an amount from 0.01 to 20% by weight of the total weight of the composition, advantageously in an amount of from 0.05 to 10% by weight, preferably from 0.1 to 5% by weight.

In particular, a TTS consisting of a patch is obtained as described for example in U.S. Pat. Nos. 5,212,199, 5,227,169, 5,747,065, 6,743,441, 7,081,249, 7,081,250, 7,081,251, 7,081,252, 7,087,241, US 2004/0057985 U.S. Pat. No. 8,420,117, US 2014/0271796, U.S. Pat. Nos. 8,802,134, 8,877,235, the disclosures of which are each incorporated herein by reference in their entirety.

A TTS consisting of a non-occlusive topical formulation for transdermal administration of oxybutynin is obtained as described for example in EP 0966972, U.S. Pat. Nos. 4,889,845, 6,962,691, US 2003/0170194, US 2005/0064037, US 2006/0147383, U.S. Pat. Nos. 7,029,694, 7,179,483, US 2009/0018190, U.S. Pat. No. 8,241,662, US 2007/0225379, US 2010/216880, U.S. Pat. Nos. 8,652,491, 7,425,340, 7,214,381, 7,470,433, US 2008/0260842, US 2014/0037713, the disclosures of which are each incorporated herein by reference in their entirety.

A TTS in form of a solution, cream, lotion, spray, ointment, gel, is manufactured by mixing a predetermined amount of oxybutynin or of a pharmaceutically acceptable salt thereof with common pharmaceutically acceptable carriers or vehicles and, optionally, with a permeation enhancer, of a gelling agent or thickening agent.

In one embodiment, a water-based gel formulation comprises 0.5-5% (w/w) of a pharmaceutically acceptable oxybutynin salt; 10-80% (w/w) of a lower ($C_2$-$C_4$) alkanol; and 0.2-2.0% of thickening agent and a basic pH regulator. The preferred short chain alcohols are ethanol and isopropanol. The preferred gelling/thickening agents include cross-linked polymer of acrylic acid with a high molecular weight, for example cross-linked copolymer of acrylic acid and ($C_{10}$-$C_{30}$)-alkyl acrylate, carboxymethylcellulose, hydroxypropylcellulose. In addition. In addition, the gel formulation comprises the permeation enhancers at from 0.01% to 20% by weight of the total weight of the composition, advantageously from 0.05% to 10% by weight, preferably from 0.1% to 5% by weight. Preferred permeation enhancer is glycerol or a monoester, diester or triester thereof, such as triacetin.

In another embodiment, a water-based gel formulation comprises 0.5-5% (w/w) of oxybutynin base; 10-80% (w/w) of a lower ($C_2$-$C_4$) alkanol; and 0.2-2.0% of a thickening agent. In addition, the gel formulation comprises the permeation enhancers at from 0.01% to 20% by weight of the total weight of the composition, advantageously at from 0.05% to 10% by weight, preferably from 0.1% to 5% by weight. The suitable permeation enhancers are those listed above, preferably being propylene glycol, mono ($C_1$-$C_4$)-alkylated diethyleneglycol, propylene glycol laurate, isopropyl myristate, and methyl lactate.

In another embodiment, a TTS in form of a sprayable composition comprises oxybutynin or a pharmaceutically acceptable salt thereof in an aqueous or non-aqueous solution. Typically, a non-aqueous sprayable composition comprises oxybutynin or a pharmaceutically acceptable salt thereof dissolved in ($C_2$-$C_4$)alkanols. Said oxybutynin is present in an amount of 0.5%-5% w/w, in respect of the total weight of the composition, from 20% to 90% w/w of a volatile silicone consisting of a linear or cyclic permethyl (tetra-deca)siloxane, such as hexamethyldisiloxane, octamethyltrisiloxane, decamethyltetrasiloxane, octamethylcyclotetrasiloxane, decamethylcyclopentasiloxane, and from 0% to 15% of a permeation enhancer as defined above. The preferred volatile silicones are hexamethyldisiloxane (for example the product provided by Dow Corning®, DC Fluid 0.65 cSt), optionally containing silicone gum (for example the product provided by Dow Corning®, DC Silmogen Carrier), and octamethyltrisiloxane.

The formulation is obtained by mixing the various compounds mentioned below until a homogeneous and clear solution is obtained and the solution can be sprayed by a mechanical sprayer which mechanically pumps the compositions from a container, preferably in a metered dose, by conventional mechanisms through a nozzle which can directed at the desired site of application. The amount of propellant gas is regulated in order to propel the exact amount of oxybutynin.

In said TTS, oxybutynin is present in an amount that allows the reduction of peripherally mediated adverse effects that would be caused by the administration of doses of CRA that are even higher that the maximal tolerated dose found for each of them in the clinical trials of said CRA.

Preferably, the oxybutynin TTS Component (a) releases 3.9-5.85 mg/day of oxybutynin, concurrently or sequentially administered in combination with even high doses of a CRA Component (b), in the treatment of Alzheimer type dementias, or symptoms thereof, in order to improve to a greater extent said disease or symptoms without adverse effects.

In a particular embodiment, the amount of oxybutynin TTS Component (a) is that which is present in the commercially available preparation for the anticholinergic therapy, i.e., releasing 3.9 mg/24 h oxybutynin.

The CRA Composition

A CRA that is able to cross the brain blood barrier of a human in order to stimulate the muscarinic cholinergic receptors in the CNS may be used as Component (b) according to the present invention.

Advantageously, the CRA used as Component (b) is one of the muscarinic cholinergic agonists that have unsuccessfully been investigated in relation to the possibility of using them for the treatment of Alzheimer type dementia.

Preferably, said CRA is selected from the group consisting of
- cis-2'-methylspiro {1-azabicyclo[2.2.2]octane-3,5'-[1,3] oxathiolane} described in U.S. Pat. Nos. 4,855,290 and 5,571,918 (cevimeline), and pharmaceutically acceptable salts and solvates thereof, especially its hydrochloride hemihydrate;
- 3-[3-(3-(3-fluorophenyl)-2-propyn-1-ylthio)-1,2,5-thiadiazol-4-yl]-1,2,5,6-tetrahydro-1-methylpyridine described in CN 1821243B and pharmaceutically acceptable salts and solvates thereof, especially its oxalate (EUK 1001);
- (E)-N-methoxy-1-(1-methyl-1,2,5,6-tetrahydropyridin-3-yl)methanimine described in U.S. Pat. No. 6,037,347 (milameline) and pharmaceutically acceptable salts and solvates thereof, especially its hydrochloride;
- 2-ethyl-8-methyl-2,8-diazaspiro[4.5]decane-1,3-dione described in U.S. Pat. No. 3,056,796 (RS-86) and pharmaceutically acceptable salts and solvates thereof, especially its hydrobromide;
- (3R)—N-methoxyquinuclidine-3-carboximidoyl cyanide described in U.S. Pat. No. 5,278,170 (sabcomeline) and pharmaceutically acceptable salts and solvates thereof, especially its hydrochloride;
- (3R)-3-(prop-2-yn-1-yloxy)-1-azabicyclo[2.2.2]octane (talsaclidine) described in U.S. Pat. No. 5,286,864, and pharmaceutically acceptable salts and solvates thereof, especially its fumarate;
- 5-[4-(hexylthio)-1,2,5-thiadiazol-3-yl]-1-methyl-1,2,3,6-tetrahydropyridine described in U.S. Pat. No. 5,041,455 (tazomeline) and pharmaceutically acceptable salts and solvates thereof, especially its hydrochloride;
- 3-(4-hexyloxy-1,2,5-thiadiazol-3-yl)-1-methyl-5,6-dihydro-2H-pyridine described in U.S. Pat. No. 5,041,455 and EP 0384288 (xanomeline) and pharmaceutically acceptable salts and solvates thereof, especially its oxalate and L-tartrate,
- 1-methylpiperidine-4-spiro-5'(2'-ethyl-1',4'-thiazoline-3'-one) (AF267) and pharmaceutically acceptable salts and solvates thereof, especially its hydrochloride (AF 267B) described in EP 0711292;
- (4-n-butyl-1-[4-(2-methylphenyl)-4-oxo-1-butyl]-piperidine (AC-42) and pharmaceutically acceptable salts and solvates thereof, especially its hydrogen chloride,
- 1-[1'-(2-methylbenzyl)-1,4'-bipiperidin-4-yl]-1,3-dihydro-2H-benzimidazol-2-one (TBPB) and pharmaceutically acceptable salts and solvates thereof;
- 4-Fluoro-6-methyl-1-[1-(tetrahydro-2H-pyran-4-yl)-4-piperidinyl]-1,3-dihydro-2H-benzimidazol-2-one and pharmaceutically acceptable salts and solvates thereof, described in WO 2007/036715), the disclosures of which are incorporated herein by reference in their entirety;
- 5-Fluoro-6-methyl-1-[1-(tetrahydro-2H-pyran-4-yl)-4-piperidinyl]-1,3-dihydro-2H-benzimidazol-2-one and pharmaceutically acceptable salts and solvates thereof, described in WO 2007/036718 and U.S. Pat. No. 8,288,412), the disclosures of which are incorporated herein by reference in their entirety;
- 4-(R)-ethyl-3-(2-methylbenzamido)-1,4'-bipiperidine-1'-carboxylate and pharmaceutically acceptable salts and solvates thereof, described in WO 2010/096703), the disclosures of which are incorporated herein by reference in their entirety;
- ethyl 3-[(3-exo)-(2-benzamidoethyl)amino]-8-azabicyclo [3.2.1]octane-8-carboxylate and pharmaceutically acceptable salts and solvates thereof, described in U.S. Pat. No. 8,697,691), the disclosures of which are incorporated herein by reference in their entirety; and
- 3-[(1S,2S)-2-hydroxycyclohexyl]-6-[(6-methylpyridin-3-yl)methyl]benzo [h]quinazolin-4(3H)-one (MK-7622), described in U.S. Pat. No. 8,883,810), the disclosures of which are incorporated herein by reference in their entirety, and pharmaceutically acceptable salts and solvates thereof, especially the fumarate or the hydrochloride.

Preferably, each of the CRAs, especially aforementioned ones, are formulated in a pharmaceutically composition, advantageously in dosage unit form.

The amount of the CRA Component (b) of the combination, e.g., a single CRA dose that is present in a unit form, may vary according to intrinsic muscarinic cholinergic receptor potency of said component. Advantageously, said dose is from 1.2-fold to 4-times and even from 1.2-fold to 6-times higher than the amount contained in a commercially available unit form or of the single CRA dose administered during clinical trials of each CRA for cholinergic therapy. Said unit form generally is for systemic use in an immediate release (IR) or extended release (ER) form, preferably in an oral IR or ER form.

In another embodiment, the amount of the CRA Component (b) of the combination, is a dose from 1.2-fold to 4-times and even from 1.2-fold to 6-times higher than the maximum amount contained in a commercially available unit form or of the maximal, single CRA dose administered during clinical trials of each CRA for cholinergic therapy. Said unit form generally is for systemic use in an IR or ER form, preferably in an oral IR or ER form.

In said combination, the CRA Component (b) is preferably selected from the group consisting of:
- cevimeline, as hydrochloride hemihydrate, in an amount of from 36 mg to 180 mg per unit form, preferably from 36 mg to 120 mg per unit form;
- milameline, as hydrochloride, in an amount of from 2.4 mg to 12 mg per unit form, preferably from 2.4 mg to 8 mg per unit form;
- xanomeline, as oxalate or as L-tartrate, in an amount of from 90 mg to 450 mg per unit form, preferably from 90 mg to 300 mg per unit form; and
- MK-7622, especially as hydrochloride or fumarate, is present in an amount of from 6 mg to 270 mg. in particular from 6 mg to 54-270 mg, normally from 54 to 180 mg, formulated in an IR or ER pharmaceutical composition, preferably for oral administration.

Preferably, the daily dose of said CRA Component (b) is higher than the mean maximal tolerated dose of said CRA determined in its clinical trials. Preferably, it is from 1.2 to 4 times and even from 1.2 to 6 times said maximal tolerated CRA dose or from 1.2 to 4 times and even 1.2 to 6 times the maximal daily dose administered to patients during the clinical trials of each CRA.

For instance, the daily dose of said CRA Component (b) is selected from the group consisting of:
- cevimeline, as hydrochloride hemihydrate, in an amount of from 108 mg to 540 mg, preferably from 108 mg to 360 mg;
- milameline, as hydrochloride, in an amount of from 9.6 mg to 48 mg, preferably from 9.6 mg to 32 mg; and
- xanomeline, as oxalate or as L-tartrate, in an amount of from 270 mg to 1,350 mg, preferably from 270 mg to 900 mg;

MK-7622, as fumarate, methanesulfonate or hydrochloride may be from 6 mg to 270 mg, advantageously from 54 mg to 270 mg, normally from 54 mg to 180 mg. formulated in an IR or ER pharmaceutical composition, preferably for oral administration.

In particular, the daily dose of cevimeline, as hydrochloride hemihydrate, is of from 108 mg to 180 mg; and the daily dose of xanomeline, as oxalate or L-tartrate, is from more than 270 mg to 1350 mg, preferably from 337.5 mg to 1350 mg, and more preferably from 337.5 to 900 mg and the daily dose of MK-7622, as fumarate, methanesulfonate or hydrochloride may be of from 25 mg to 180 mg.

For such an administration, the CRA is formulated in a pharmaceutical composition in unit form. Said unit form may be a tablet for direct ingestion or for oral dissolution, a capsule, a pre-measured volume of a liquid solution or suspension for oral administration in combination with an oxybutynin TTS. In said unit form, the CRA, as free base or as a pharmaceutically acceptable salt or solvate thereof, may be mixed with a pharmaceutical carrier in a pharmaceutical composition, in IR or in ER form, according to known technologies.

Carriers for IR tablets include for example starches, cellulose and derivatives thereof; lubricants such as talc, stearic acid or magnesium stearate; diluents such as talc, powdered cellulose, lactose, starches such as maize or corn starch, mannitol, sorbitol; disaggregating agents such as microcrystalline cellulose or crospovidone; lubricant such as polyethylene glycol or magnesium stearate; ligands such as methylcellulose, sodium carboxymethylcellulose, alginic acid, alginates; sweeteners, such as sucrose, dextrose, mannitol, saccharin; or flavoring agents such as natural or synthetic oils.

Carriers for orally disintegrating tablets include for example lubricants, aggregating, sweetening, flavoring or disaggregating agents as well as agents improving the buccal mucosa absorption of components (a) and (b) such as sorbitol, mannitol, lactose and cellulose.

The sweeteners contained in the orally disintegrating tablets may be natural, optional reduced sugars such as sucrose, dextrose, xylitol, mannitol or sorbitol, or synthetic product such as sodium saccharine or aspartame.

The flavoring agents are pharmaceutically acceptable flavors and tastes of synthetic and natural oils, the latter extracted from plants, leaves, flowers, fruits and their combinations, such as cinnamon, peppermint, anise and citron leaves, bitter almond, citrus fruits, in particular orange and/or lemon, linden and grapefruit oils. Also chocolate, vanilla or eucalyptus flavor and essences of fruit, in particular apple, pear, peach, strawberry, cherry, apricot, orange, lemon and grapes may be advantageously used.

The sweeteners contained in the orally disintegrating tablets and the liquid suspensions or solutions may be natural, optional reduced sugars such as sucrose, dextrose, xylitol, mannitol or sorbitol, or synthetic product such as sodium saccharine or aspartame.

The flavoring agents are pharmaceutically acceptable flavors and tastes of synthetic and natural oils, the latter extracted from plants, leaves, flowers, fruits and their combinations, such as cinnamon, peppermint, anise and citron leaves, bitter almond, citrus fruits, in particular orange and/or lemon, linden and grapefruit oils. Also chocolate, vanilla or eucalyptus flavor and essences of fruit, in particular apple, pear, peach, strawberry, cherry, apricot, orange, lemon and grapes may be advantageously used.

Carriers for ER formulations include retardant materials such as acrylic and methacrylic acid polymers and copolymers; cellulose derivatives such as hydroxypropylmethylcellulose, hydroxyethylcellulose, hydroxypropylethylcellulose, hydroxypropylcelluloses, methylcellulose, ethylcellulose, or sodium carboxymethylcellulose; gums; waxes; glycerides or aliphatic alcohols or a mixture thereof.

The AChEIs

According to the present invention, the combination may contain, as a further component, Component (c) an AChEI also formulated in a pharmaceutical composition. Said AChEI may include, but is not limited to, 1,2,3,4-tetrahydro-9-acridinamine (tacrine) and pharmaceutically acceptable salts and solvates thereof, (1R,9S,13E)-1-amino-13-ethylidene-11-methyl-6-azatricyclo[7.3.1.0$^{2,7}$]trideca-2(7),3,10-trien-5-one (huperzine A, (±)-2,3-dihydro-5,6-dimethoxy-2-[[1-(phenylmethyl)-4-piperidinyl]methyl]-1H-inden-1-one (donepezil) and pharmaceutically acceptable salt and solvates thereof, (S)—N-Ethyl-N-methyl-3-[1-(dimethylamino)ethyl]-phenyl carbamate (rivastigmine) and pharmaceutically acceptable salts and solvates thereof, or 4aS,6R,8aS-3-methoxy-11-methyl-4a,5,9,10,11,12-hexahydroxy-6H-benzofuro[3a,3,2-e,f]benzazepin-6-ol (galantamine) and pharmaceutically acceptable salts and solvates thereof.

The AChEI Component (c) when included in the combination with Component (a), Component (b) as described herein, may be present in the amount currently used for treating Alzheimer disease, or also in a higher dose.

Said AChEIs may be used in brand preparation. For example, rivastigmine may be orally administered by using EXELON® immediate-release 3 mg or 6 mg-capsules or by applying EXELON® patches releasing 4.6 mg/24 hours, 9.5 mg/24 hours, or 13.3 mg/24 hours on the subject's skin.

Huperzine A may be used as a commercial preparation, by orally administering 0.05-0.2 mg immediate-release oral unit forms such as tablets or capsules.

Donepezil hydrochloride may be also used as a brand preparation, for example by orally administering ARICEPT® immediate-release 5 mg- or 10 mg-tablets or the 23-mg tablets. In particular, donepezil hydrochloride may be orally administered, in combination with the above-illustrated MCRA and nsPAChA, at a daily dose preferably of from 5 mg to 60 mg.

Galantamine, as hydrobromide, may be also administered as a brand preparation, for example by orally administering RAZADYNE® immediate-release 8 mg- or 12 mg-tablets or RAZADYNE® ER 8 mg-, 16 mg- or 24 mg-capsules. In particular, galantamine hydrobromide may be orally administered, in combination with the above-illustrated oxybutynin TTS, at a daily dose up to 42 mg.

Among the particularly preferred AChEIs, in the combinations of the present invention donepezil hydrochloride is present at a dose of from 5 mg to 60 mg, advantageously from 15 mg to 60 mg; rivastigmine, as hydrogen tartrate, is present, in a composition for oral administration, at a dose of from 3 mg to 15 mg, advantageously from 9 mg to 15 mg; as the free base, rivastigmine is present in patch releasing from 4.6 mg/24 h to 52 mg/24 h rivastigmine, advantageously from 9.6 mg/24 h to 33.25 mg/24 h, normally from 13.3 mg/24 h to 33.25 mg/24 h; and galantamine (as hydrobromide, is present in an amount of from 8 mg to 36 mg in an IR formulation or from 24 mg to 42 mg in an ER formulation.

Preferred Embodiments

An advantageous combination according to the present invention comprises, as Components, (a) a muscarinic receptor antagonist selected from the group consisting of oxybutynin and pharmaceutically acceptable salts and solvates thereof in a TTS; and (b) a muscarinic receptor agonist consisting of a cholinergic receptor agonists (CRA) selected from the group consisting of
- 1-methylpiperidine-4-spiro-5'(2'-ethyl-1',4'-thiazoline-3'-one) and pharmaceutically acceptable salts and solvates thereof, especially its hydrochloride;
- cevimeline and pharmaceutically acceptable salts and solvates thereof, especially its hydrochloride hemihydrate;
- 3-[3-(3-(3-fluorophenyl)-2-propyn-1-ylthio)-1,2,5-thiadiazol-4-yl]-1,2,5,6-tetrahydro-1-methylpyridine;
- milameline and pharmaceutically acceptable salts and solvates thereof, especially its hydrochloride;
- 2-ethyl-8-methyl-2,8-diazaspiro[4.5]decane-1,3-dione and pharmaceutically acceptable salts and solvates thereof, especially its hydrobromide;
- sabcomeline and pharmaceutically acceptable salts and solvates thereof, especially its hydrochloride;
- talsaclidine and pharmaceutically acceptable salts and solvates thereof, especially its fumarate;
- tazomeline and pharmaceutically acceptable salts and solvates thereof, especially its hydrochloride; and
- xanomeline and pharmaceutically acceptable salts and solvates thereof, especially its oxalate and L-tartrate;
- MK-7622 and pharmaceutically acceptable salts and solvates thereof, especially its fumarate, monomethanesulfonate and hydrochloride, in an oral IR or ER formulation.

A pharmaceutical combination comprising,

Component (a) a muscarinic receptor antagonist selected from the group consisting of oxybutynin and pharmaceutically acceptable salts and solvates thereof in a TTS; preferably, the oxybutynin is released at a rate of from 3.9 mg/24 h to 5.2 mg/24 h; and Component (b) a muscarinic receptor agonist consisting of a CRA selected from the group consisting of:
- cevimeline, as hydrochloride hemihydrate, in an amount of from 36 mg to 180 mg per unit form, preferably from 36 mg to 120 mg per unit form;
- milameline, as hydrochloride, in an amount of from 2.4 mg to 12 mg per unit form, preferably from 2.4 mg to 8 mg per unit form; and
- xanomeline, as oxalate or as L-tartrate, in an amount of from 90 mg to 450 mg per unit form, preferably from 90 mg to 300 mg per unit form;
- MK-7622, as fumarate, methanesulfonate or hydrochloride, in an amount of from 6 mg to 270 mg, preferably from 25 mg to 180 mg, formulated as a pharmaceutical combination in an ER or IR pharmaceutical composition.

Preferably, the pharmaceutical combination is in an oral pharmaceutical composition.

Alternatively, the daily dose of said CRA Component (b) is higher than the mean maximal tolerated dose of said CRA determined in its clinical trials. Preferably, it is from 1.2 to 4 times and even from 1.2 to 6 times said maximal tolerated CRA dose or from 1.2 to 4 times and even 1.2 to 6 times the maximal daily dose administered to patients during the clinical trials of each CRA.

For instance, the daily dose of said CRA Component (b) is selected from the group consisting of:
- cevimeline, as hydrochloride hemihydrate, from 108 mg to 540 mg, preferably from 108 mg to 360 mg;
- milameline, as hydrochloride, from 9.6 mg to 48 mg, preferably from 9.6 mg to 32 mg; and
- xanomeline, as oxalate or as L-tartrate, from 270 mg to 1,350 mg, preferably from 270 mg to 900 mg;
- MK-7622, as fumarate, methanesulfonate or hydrochloride, from 6 mg to 270 mg, preferably from 25 mg to 180 mg, each formulated in an IR or ER pharmaceutical composition, preferably for oral administration.

In particular, the daily dose of cevimeline, as hydrochloride hemihydrate, is of from 108 mg to 180 mg; and the daily dose of xanomeline, as oxalate or L-tartrate, is from more than 270 mg to 1350 mg, preferably from 337.5 mg to 1350 mg, and more preferably from 337.5 to 900 mg and the daily dose of MK-7622, as fumarate, methanesulfonate or hydrochloride, is from 25 mg to 180 mg.

More preferably, the oxybutynin TTS releases 3.9 mg/24 h oxybutynin.

According to a further embodiment, an advantageous combination according to the present invention comprises, as Components, (a) a muscarinic receptor antagonist selected from the group consisting of oxybutynin in a patch releasing from 3.9 mg/24 h to 7.8 mg/24 h oxybutynin;

(b) a muscarinic receptor agonist consisting of MK-7622, as fumarate, methanesulfonate or hydrochloride, in an amount of from 6 mg to 270 mg, formulated in a pharmaceutical composition in admixture with a pharmaceutical carrier; and (c) an AChEI consisting of donepezil hydrochloride, in an amount of from 5 mg to 60 mg, formulated in a pharmaceutical composition in admixture with a pharmaceutical carrier.

According to a second aspect of this embodiment, an advantageous combination according to the present invention comprises, as Components, (a) a muscarinic receptor antagonist selected from the group consisting of oxybutynin in a patch releasing from 3.9 mg/24 h to 7.8 mg/24 h oxybutynin;

(b) a muscarinic receptor agonist consisting of MK-7622, as fumarate, methanesulfonate or hydrochloride, in an amount of from 6 mg to 270 mg, formulated in a pharmaceutical composition in admixture with a pharmaceutical carrier; and (c) an AChEI consisting of rivastigmine, in patch releasing from 4.6 mg/24 h to 32.5 mg/24 h rivastigmine.

According to a third aspect of this embodiment, another advantageous combination according to the present invention comprises oxybutynin/rivastigmine fixed-dose combination wherein Component (a) and Component (c) are in a single patch containing the two active ingredients in admixture each other in the same patch or separated in the same patch in two different patches, each delivering the aforementioned oxybutynin Component (a) and rivastigmine Component (c) daily doses.

The Use

As set forth herein above, Component (a) and Component (b) may be administered concurrently or sequentially to a patient suffering from Alzheimer type dementia. In particular, Component (a) and Component (b) can be administered in a specific dosage regimen to treat Alzheimer type dementia, Component (a) and Component (b) being administered simultaneously or sequentially to one another.

Thus, according to another of its aspects, the present invention provides a combination comprising:
Component (a) a muscarinic receptor antagonist which is an oxybutynin transdermal therapeutic system; and
Component (b) a muscarinic receptor agonist selected from the group consisting of cholinergic receptor agonists (CRA),
for use in the treatment of Alzheimer type dementia.

The muscarinic receptor antagonist used as Component (a), their properties and doses are described in the above "The Oxybutynin Transdermal System" section.

The CRAs used as Component (b), their properties and doses are described in the above "The CRA Composition" section.

For use, Component (a) and Component (b) may be formulated as described in the above "The Oxybutynin Transdermal System" and "The CRA Composition" sections.

According to another embodiment, the present invention provides a method for treating Alzheimer type dementia, which comprises administering to a patient in need of said treatment a pharmaceutical combination comprising:
Component (a) a muscarinic receptor antagonist selected from the group consisting of oxybutynin and pharmaceutically acceptable salts and solvates thereof in a TTS; and
Component (b) a muscarinic receptor agonist selected from the group consisting of cholinergic receptor agonists (CRA).

Component (a) and Component (b) may be administered combination concurrently or sequentially.

The muscarinic receptor antagonist used as Component (a), their properties and doses are described in the above "The Oxybutynin Transdermal System" section.

The CRAs used as Component (b), their properties and doses are described in the above "The CRA Composition" section.

For use, Component (a) and Component (b) may be formulated as described in the above "The Oxybutynin Transdermal System" and "The CRA Composition" sections.

In particular, for the above use, an advantageous combination comprises:
Component (a) a muscarinic receptor antagonist selected from the group consisting of oxybutynin and pharmaceutically acceptable salts and solvates thereof in a TTS; and
Component (b) a muscarinic receptor agonist consisting of a cholinergic receptor agonists (CRA) selected from the group consisting of
1-methylpiperidine-4-Spiro-5'(2'-ethyl-1',4'-thiazoline-3'-one) and pharmaceutically acceptable salts and solvates thereof, especially its hydrochloride;
cevimeline and pharmaceutically acceptable salts and solvates thereof, especially its hydrochloride hemihydrate;
3-[3-(3-(3-fluorophenyl)-2-propyn-1-ylthio)-1,2,5-thiadiazol-4-yl]-1,2,5,6-tetrahydro-1-methylpyridine;
milameline and pharmaceutically acceptable salts and solvates thereof, especially its hydrochloride;
2-ethyl-8-methyl-2,8-diazaspiro[4.5]decane-1,3-dione and pharmaceutically acceptable salts and solvates thereof, especially its hydrobromide;
sabcomeline and pharmaceutically acceptable salts and solvates thereof, especially its hydrochloride;
talsaclidine and pharmaceutically acceptable salts and solvates thereof, especially its fumarate;
tazomeline and pharmaceutically acceptable salts and solvates thereof, especially its hydrochloride; and
xanomeline and pharmaceutically acceptable salts and solvates thereof, especially its oxalate and L-tartrate;
MK-7622 and pharmaceutically acceptable salts and solvates thereof, especially its fumarate, methanesulfonate or hydrochloride;
in an IR or ER formulation in unit form, preferably an oral IR or ER formulation in unit form.

Advantageously, said Component (a) and said Component (b) are also combined with an AChEI component (c), as illustrated herein above.

The following examples are included for illustrative purposes only, and are not intended to limit the scope of the invention.

Example 1

Study 1—Establishment of the Dose-Response to Xanomeline in a Mouse Model of Diarrhea.

Male Swiss mice (4-6 weeks old), N=10 per treatment group were used, and treated intra-peritoneally (i.p.) with either vehicle (vehicle group) or increasing doses of xanomeline, a representative muscarinic agonist. Mice were randomly assigned to one of two experimental groups (vehicle; or increasing doses of xanomeline). Each animal was identified by its group name, cage number, series (day) of experiment, and number (1 to 10) written with permanent ink on the tail.

Mice were placed individually in cages without any bedding materials. During the experiment the number of fecal pellets were counted at different time-points, starting one hour before the time of the administration of the test compound (T0), as outlined below:

T−1 h to T0: counting of the accumulated fecal pellets excreted.

T0: administration of the test compound.

T0 to T+2 h: counting of the accumulated fecal pellets excreted.

T+2 h to T+4 h: counting of the accumulated fecal pellets excreted.

The total number of fecal pellets for each mouse was counted over time. An analysis of variance (ANOVA) was performed on the results. Fisher's Protected Least Significant Difference was used for pairwise comparisons; p values≤0.05 were considered significant. Grubbs' test (http://www.graphpad.com/quickcalcs/Grubbs1.cfm) was used to detect outliers for each parameter in each experimental group.

Results confirmed that xanomeline i.p. (0.3 to 30 mg/kg) dose-dependently causes diarrhea.

Study 2—Antagonism of Xanomeline-Induced Diarrhea in Mice by Oxybutynin

Male Swiss mice (4-6 weeks old), N=10 per treatment group were used. Animals were pretreated with i.p. oxybutynin (a representative peripheral muscarinic receptor antagonist) or vehicle; 30 minutes later animals were treated with xanomeline at a dose of 30 mg/kg that caused diarrhea (as determined in Experiment 1). The dose of oxybutynin ordinarily ranged from 0.3 to 30 mg/kg.

Mice were placed individually in cages without any bedding materials. During the experiment the number of fecal pellets was counted at different time-points as outlined below:

T−1 h to T0: counting of the accumulated fecal pellets excreted.

T0: administration of oxybutinin.

T30 min: administration of vehicle or xanomeline.

T 30 min to T 2.5 h: counting of accumulated fecal pellets excreted.

T+2.5 h to T+4.5 h: counting of accumulated fecal pellets excreted.

The total number of fecal pellets for each mouse was counted over time. An analysis of variance (ANOVA) was performed on the results. Fisher's Protected Least Significant Difference was used for pairwise comparisons. The p value≤0.05 were considered significant. Grubbs' test (http//www at graphpad.com/quickcalcs/Grubbs1.cfm) was used to detect outliers for each parameter in each experimental group.

Results showed that oxybutynin dose-dependently antagonized the diarrhea induced by xanomeline, thus confirming that the representative nsPAChA oxybutynin suppresses the adverse effects of the representative muscarinic antagonist xanomeline.

Example 2

Evaluation of Cognition with Oxybutynin and Xanomeline in the T-maze Alternation Task in Mice The T-maze continuous alternation task (T-CAT) is useful as model for studying compounds with cognitive enhancing properties. The T-maze consists of 2 choice arms and 1 start arm mounted to a square center. Manual doors are provided to close specific arms during the force choice alternation task.

Male Swiss mice (4-6 weeks old), N=10 per treatment group were used, and were pretreated with:

Oxybutynin at the dose that blocked fecal pellet excretion in Study 2 of Example 1.

Thirty minutes later mice were treated with either vehicle or one of 4 doses of xanomeline:

the highest dose that did not cause diarrhea;

a dose that caused diarrhea.

Mice were randomly assigned to one of the different experimental treatment groups. Each animal was identified by its group name, cage number, series (day) of experiment, and number (1 to 10) written with permanent ink on the tail.

The T-maze apparatus is made of gray Plexiglas with a main stem (55 cm long☐10 cm wide☐20 cm high) and two arms (30 cm long☐10 cm wide☐20 cm high) positioned at 90 degree angle relative to the main stem. A start box (15 cm long☐10 cm wide) is separated from the main stem by a guillotine door. Horizontal doors are also provided to close specific arms during the force choice alternation task.

The experimental protocol consisted of one single session, which started with 1 "forced-choice" trial, followed by 14 "free-choice" trials. In the first "forced-choice" trial, animals were confined for 5 seconds to the start arm and then were released while either the left or the right goal arm was blocked by the horizontal door. Animals then negotiated the maze, eventually entering the open goal arm, and returned to the start position. Immediately after the return of the animals to the start position, the left or right goal door was opened and the animals were allowed to choose freely between the left and right goal arm ("free choice trials). An animal was considered as having entered in arm when it placed its four paws in the arm. A session was terminated and animals were removed from the maze as soon as 14 free-choice trials had been performed or 10 min had elapsed, whichever event occurred first.

The apparatus was cleaned between each animal using 40% ethanol. Urine and feces were removed from the maze. During the trials, animal handling and the visibility of the operator was minimized as much as possible.

The percentage of alternation over the 14 free-choice trials was determined for each mouse and was used as an index of working memory performance. This percentage is defined as entry in a different arm of the T-maze over successive trials (i.e., left-right-left-right, etc).

Analysis of variance (ANOVA) was performed on the results. Fisher's Protected Least Significant Difference was used for pairwise comparisons; p values≤0.05 were considered significant. The drug-induced improvement of memory was calculated by setting the respective response of the saline/vehicle as 100% and that of the test group as 0% reversion. Grubbs' test (http address www at graphpad.com/quickcalcs/Grubbs1.cfm) was used to detect outliers for each parameter in each experimental group.

Results showed a dose-dependent increase in performance in the T-maze in animals treated with i.p. xanomeline. At the higher dose, however, animals were too sick to perform the test. Pretreatment with i.p. oxybutynin restored the animals' ability to perform the T-maze test.

The invention claimed is:

1. A pharmaceutical combination comprising:

Component (a) a muscarinic receptor antagonist selected from the group consisting of oxybutynin and pharmaceutically acceptable salts and solvates thereof in a transdermal therapeutic system (TTS); and Component (b) a muscarinic receptor agonist selected from the group consisting of cholinergic receptor agonists;

wherein said Component (a) is in the transdermal therapeutic system (TTS) releasing from 3.9 mg/24 h to 5.2 mg/24 h of oxybutynin; and, wherein said muscarinic receptor agonist Component (b) is 3-(4-hexyloxy-1,2,5-thiadiazol-3-yl)-1-methyl-5,6-dihydro-2H-pyridine (xanomeline) and pharmaceutically acceptable salts and solvates thereof.

2. The pharmaceutical combination of claim 1, wherein said cholinergic receptor agonist Component (b) is an oral IR or ER composition.

3. The pharmaceutical combination of claim 1, wherein said TTS releases 3.9 mg/24 h oxybutynin.

4. The pharmaceutical combination of claim 2, wherein said muscarinic receptor agonist Component (b) is xanomeline, as oxalate or as L-tartrate, in an amount of from 90 mg to 450 mg per unit form.

5. The pharmaceutical combination according to any one of claims 1, 2, 3 or 4, wherein said Component (b) is formulated in a pharmaceutical composition in dosage unit form, in admixture with a pharmaceutical carrier.

6. The pharmaceutical combination of claim 1, wherein said Component (a) is in the TTS releasing from 3.9 mg/24 h to 5.2 mg/24 h oxybutynin and said Component (b) is xanomeline, as oxalate or as L-tartrate, in an amount of from 90 mg to 450 mg per unit form.

* * * * *